United States Patent [19]

Torihara et al.

[11] Patent Number: 4,959,393

[45] Date of Patent: Sep. 25, 1990

[54] SKIN DEPIGMENTAL AGENT

[75] Inventors: Masahiro Torihara, Kurashiki; Yoshin Tamai, Shibata; Manzo Shiono; Kenji Tasaka, both of Okayama, all of Japan

[73] Assignee: Kuraray Company, Ltd., Kurashiki, Japan

[21] Appl. No.: 343,571

[22] Filed: Apr. 27, 1989

[30] Foreign Application Priority Data

May 9, 1988 [JP] Japan .................. 63-113286

[51] Int. Cl.$^5$ .......................... A61K 31/045
[52] U.S. Cl. .......................... 514/724
[58] Field of Search ...................... 514/724

[56] References Cited

U.S. PATENT DOCUMENTS 3,933,925 1/1975 Greco .

FOREIGN PATENT DOCUMENTS 2152442 9/1971 France .
1371782 10/1970 United Kingdom .

OTHER PUBLICATIONS

Chemical Abstracts, vol. 85, 1976, p. 308, abstract no. 182272a, Columbus, Ohio, US; & JP-A-76 101 138 (Ichimaru Co. Ltd.), 07-09-1976, *Abstract*.

Primary Examiner—Stanley J. Friedman
Attorney, Agent, or Firm—Oblon, Spivak, McClelland, Maier & Neustadt

[57] ABSTRACT

A skin depigmental agent characterized by comprising a resorcinol derivative having a linear alkyl group is provided.

6 Claims, No Drawings

SKIN DEPIGMENTAL AGENT

BACKGROUND OF THE INVENTION

1. Field of the Invention

This invention relates to an agent having a high skin depigmental effect.

2. Description of the Related Art

The mechanism of formation of spots or freckles on the skin is considered as follows: the activity of tyrosinase is promoted by the action of melanosite-irritative hormone or UV rays to have melanin eventually formed as chromatism in the skin. There is a strong demand for agents which enable acquired deposition sites, such as spots or freckles, to be restored to a normal skin color. For this purpose, a variety of agents and methods have been developed and put on the market until now. For instance, there are adopted a method wherein vitamin C (L-ascorbic acid) having good reducing ability is dosed in large amounts, a method of injecting glutathione or the like, a method using peroxides, such as hydrogen peroxide, zinc peroxide, sodium peroxide and the like, which are believed to have the bleaching action of melamine, and a method wherein vitamin C or cysteine is applied to local sites in the form of an ointment, cream, lotion or the like. In Europe and America, a hydroquinone agent has been used as a medicine [A.B. Lerner and Fitzpatrick, Biochemistry of Melanin Formation, 30, 91(1950)].

Vitamin C has a problem with respect to stability and becomes so unstable in water-containing systems that they will cause changes in odor and color. Thiol compounds such as glutathione and cysteine do not exhibit a satisfactory depigmental effect since the development of the effect is very slow.

SUMMARY OF THE INVENTION

Under these circumstances in the art, we have made intensive studies on tyrosinase activity-inhibiting agents in order to develop a skin depigmental agent having good depigmental effects in consideration of the formation mechanism of melanin. As a result, it has been found that a certain type of resorcinol derivative has a very good tyrosinase activity-inhibiting effect. The present invention has been accomplished based on the above finding.

According to the invention, there is provided a skin depigmental agent which comprises, as an effective component, a resorcinol derivative of the following formula (1)

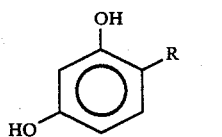

(1)

wherein R represents a linear alkyl group having from 2 to 12 carbon atoms with or without substitution of one hydrogen atom of the linear alkyl group with a methyl group.

DESCRIPTION OF THE PREFERRED EMBODIMENTS

In the above formula (1), the unsubstituted linear alkyl group represented by R and having from 2 to 12 carbon atoms include an ethyl group, a propyl group, a butyl group, a pentyl group, a hexyl group, a heptyl group, an octyl group, a nonyl group, a decyl group, an undecyl group and a dodecyl group. These linear alkyl groups may be substituted with a methyl group at one hydrogen atom thereof. Specific examples of the substituted alkyl group include an isopropyl group, an isobutyl group, an isoamyl group, a 2-methylhexyl group and the like. The most preferable R is an isoamyl group.

The resorcinol derivatives of the formula (1) are known compounds and can be readily obtained, for example, by a method wherein a saturated carboxylic acid and resorcinol are condensed in the presence of zinc chloride and the resultant condensate is reduced with zinc amalgam/hydrochloric acid (Lille. J. Bitter, LA. Peiner. V, Tr. Nauch-Issled. Inst. slantsev 1969, No. 18, 127), or by a method wherein resorcinol and a corresponding alkyl alcohol are reacted in the presence of an alumina catalyst at a high temperature of from 200 to 400° C (British Patent No. 1,581,428).

The amount of the resorcinol derivative of the formula (1) is in the range of from 0.01 wt% to 15 wt%, preferably from 0.1 to 10 wt%, of the total amount of a cosmetic composition.

The skin depigmental agent of the invention is usually used along with a cosmetic base. The cosmetic bases may be any bases which are ordinarily used for skin depigmental agents and are not thus critical. Specific preparations of the cosmetics to which the skin depigmental agent of the invention is applicable include creams, ointments, emulsions, lotions, oils, packs and the like. Cream bases are, for example, beeswax, cetyl alcohol, stearic acid, glycerine, propylene glycol, propylene glycol monostearate, polyoxyethylene cetyl ether and the like. Lotion bases include, for example, oleyl alcohol, ethanol, propylene glycol, glycerine, lauryl ether, sorbitan monolaurate and the like.

The skin depigmental agent of the invention is used along with these starting materials to prepare an intended cosmetic, such as a cream, emulsion, lotion or the like, by a usual manner. In the skin depigmental agent of the invention, there may be added to the ordinarily employed cosmetic bases UV absorbers, UV diffusing agents typical of which is finely divided titanium oxide, various medically effective ingredients such as allantoin, a placenta extract and the like, other thickeners, plasticizers, calamine, pigments, antioxidants, chelating agents, perfumes and the like.

EXAMPLES

The utility of the skin depigmental agent according to the invention is more particularly described.

PREPARATORY EXAMPLE 1

71.85 g of thionyl chloride was dropped into 23.23 g of n-caproic acid at room temperature in 1 hour, followed by agitation for 5 hours.

After completion of the reaction, excess thionyl chloride was distilled off. The resultant residue was charged into a suspension of 81.77 g of zinc chloride in 150 ml of methylene chloride cooled down to 10° C., to which 26.42 g of resorcinol was added, followed by reaction for 30 minutes and returning to room temperature for reaction for further 8 hours. 100 ml of 5% HCl was added to the reaction solution, which was extracted twice with 100 ml of isopropyl ether.

After removal of the isopropyl ether by distillation, the residue was purified by column chromatography (silica gel, n-hexane/ethyl acetate=3/1 on the volume basis).

Subsequently, 30.0 g of zinc powder was mixed with 2.50 g of mercuric chloride, 1.5 ml of concentrated hydrochloric acid and 38 ml of water and shaken for 5 minutes, followed by decantation to discard the aqueous phase. Thereafter, 20 ml of water, 45 ml of concentrated hydrochloric acid, 25 ml of toluene and 14.6 g of the previously obtained n-hexanoyl resorcinol were added in this order, followed by refluxing under heating conditions for 30 hours. During the refluxing, 12.5 ml of concentrated hydrochloric acid was added four times every 6 hours in order to keep the concentration of the acid. The reaction solution was cooled down to room temperature and subjected to liquid separation. The resultant aqueous phase was extracted three times with 50 ml of isopropyl ether and combined with the organic phase, followed by washing with 100 ml of water. The solvent was distilled off by means of an evaporator and the residue was crystallized from n-hexane to obtain 4.3 g of n-hexyl resorcinol as colorless needle crystals.

In the same manner as described above, there were prepared methyl resorcinol, ethyl resorcinol, n-butyl resorcinol, isoamyl resorcinol, n-octyl resorcinol and n-dodecyl resorcinol.

EXAMPLES 1–12

(DEPIGMENTAL EFFECT)

It is experimentally shown that the resorcinol derivatives of the formula (1) inhibit the tyrosinase activity which takes part in the formation of melanin.

Tyrosinase is a copper-containing enzyme which controls synthesis of melanin from starting tyrosine. This enzyme is considered to act as a catalyst for the formation of dopa, dopaquinone and indole-5,6-quinone which are, respectively, intermediates for the synthesis of melanin. We measured activities of the resorcinol derivatives of the formula (1) on inhibition of the formation reactions of the former two intermediates, i.e. the formation reaction of dopa (tyrosine hydroxylase) from tyrosine and the formation reaction of dopa quinone (dopa oxidase) from the dopa. From this, the activity on the tyrosinase activity inhibition was determined.

TEST METHOD (1) Measurement of Tyrosine Hydroxylation Activity 3 ml of a substrate (L-tyrosine, $1 \times 10^{-4}$M) solution was placed in a cell of an absorptiometer, to which 30 l of either a resorcinol derivative or hydroquinone for comparison each having a concentration of 100 times a final concentration was added and well mixed. The presence or absence of UV absorptions of the substrate and the substance to be detected was confirmed, after which 50 l of tyrosinase (Mushroom, 200 units, made by Sigma Co., Ltd.) was added for starting the reaction. The variation in absorbance at 280 nm which is a maximum absorption of L-dopa was measured. The tyrosine hydroxylation activity was indicated a nmol dopa/-min/mg of protein. The amount of the protein was measured according to Lowry's method.

| | Substance to Be Detected | Activity |
|---|---|---|
| Control Experiment No. | — | 1.83 |
| 1 | 4-ethyl resorcinol | 0.00 |
| 2 | 4-n-propyl resorcinol | 0.00 |
| 3 | 4-isobutyl resorcinol | 0.00 |
| 4 | 4-n-pentyl resorcinol | 0.00 |
| 5 | 4-n-octyl resorcinol | 0.00 |
| 6 | 4-n-dodecyl resorcinol | 0.33 |
| Comparative Experiment No. | | |
| 1 | 4-methyl resorcinol | 1.78 |
| 2 | hydroquinone | 0.00 |

(2) Measurement of Dopa Oxidation Activity

The general procedure of Measurement (1) was repeated except that L-dopa ($5 \times 10^{-3}$M) was used as a that produced dopa chrome was measured at a wavelength of 475 nm, and that 10 units of tyrosinase were used.

The dopa oxidation activity was indicated as μmol of dopa chrome/min/mg of protein.

| | Substance to Be Detected | Activity |
|---|---|---|
| Control Experiment No. | — | 15.80 |
| 7 | 4-ethyl resorcinol | 7.44 |
| 8 | 4-n-propyl resorcinol | 0.00 |

-continued

| | Substance to Be Detected | Activity |
|---|---|---|
| 9 | 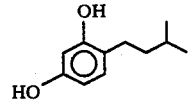 | 0.00 |
| 10 | 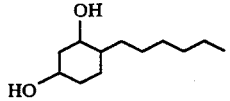 | 0.00 |
| 11 | 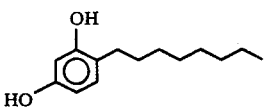 | 0.00 |
| 12 | 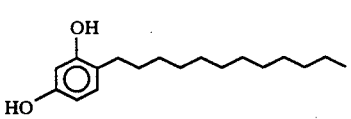 | 7.19 |
| Comparative Experiment No. | | |
| 3 | 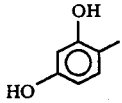 | 16.81 |
| 4 | hydroquinone | 26.94 |

TEST EXAMPLE 1
(VARIABILITY TEST)

Isoamyl resorcinol was subjected to an Ames test using salmonella typhimuria, revealing that there was no variability.

TEST EXAMPLE 2
(ACUTE TOXICITY)

Resorcinol derivatives or hydroquinone for comparison was dissolved in a physiological saline solution, which was subjected to peroral (p.o.), intraperitoneal (i.p.) and subcutaneous (s.c.) dosages against a group of ten ddy male mice. The life or death of the mice before 24 hours was observed. The value of $LD_{50}$ was calculated according to the Litchfield-Wilcoxom method using the above results. The results are shown in the table below.

| Compound | $LD_{50}$ (mg/kg) | | |
|---|---|---|---|
| | i.p. | s.c. | p.o. |
|  | 334.8 | > 500 | > 500 |
| 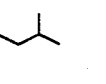 | 268.8 | > 500 | > 500 |
| hydroquinone | 144.0 | 338.8 | 489.0 |

| Formulation Example 1 (Lotion) | |
|---|---|
| Propylene glycol | 10.0 |
| Ethyl alcohol | 20.0 |
| Liquid paraffin | 2.0 |
| Polyoxyethylene(30) hardened castor oil | 1.0 |
| 4-Isoamyl resorcinol | 8.0 |
| Polyethylene glycol | 5.0 |
| Citric acid | 0.2 |
| Sodium dihydrogen phosphate | 0.3 |
| Allantoin | 0.05 |
| EDTA-2Na | 0.05 |
| Antioxidant | 0.02 |
| Perfume | 0.2 |
| Purified water | 53.18 |
| Formulation Example 2 (Cream) | |
| Solid paraffin | 2.0 |
| Stearyl alcohol | 4.0 |
| Squalane | 2.0 |
| Liquid paraffin | 6.0 |
| Glyceryl monostearate | 2.5 |
| Polyoxyethylene sorbitan monostearate | 2.5 |
| Ethyl alcohol | 9.0 |
| Propylene glycol | 8.0 |
| 4-Isoamyl resorcinol | 4.0 |
| 2-Hydroxy-4-methoxybenzophenone | 3.0 |
| Hydrophobically treated fine powder of titanium oxide | 5.0 |
| purified water | 52.0 |
| Formulation Example 3 (Foundation) | |
| Hydrophobically treated fine powder of Titanium oxide | 7.0 |
| Triglyceride of stearic acid | 2.0 |
| 2-Octyldodecyl oleate | 8.0 |
| Liquid paraffin | 3.0 |
| Cetyl alcohol | 5.0 |
| Candelilla wax | 2.0 |
| 4-Isoamyl resorcinol | 5.0 |
| Polyoxyethylene(25) monostearate | 2.0 |
| Sorbitan monostearate | 1.0 |
| Iron oxide yellow | 1.3 |
| Iron oxide red | 0.8 |
| Polyethylene glycol | 4.0 |
| Methylparaben | 0.2 |
| Perfume | 0.2 |
| Purified water | 58.5 |
| Formulation Example 4 (Powder) | |
| Talc | 80.0 |
| crystalline cellulose | 5.0 |
| Ultramarine blue | 1.0 |
| Spherical calcium silicate | 3.0 |
| Finely divided titanium oxide | 3.5 |
| 4-Isoamyl resorcinol | 3.0 |
| Squalane | 4.5 |
| Formulation Example 5 (Lotion) | |
| Propylene glycol | 15.0 |
| L-menthol | 0.1 |
| Ethanol | 15.0 |
| Polyoxyethylene(30) hardened castor oil | 0.5 |
| Anti-inflammatory agent | 1.0 |
| 4-Isoamyl resorcinol | 1.5 |
| Isoferulic acid triethanolamine | 3.5 |
| Perfume | 0.3 |
| Purified water | 65.1 |
| Formulation Example 6 (Pack) | |
| Polyvinyl alcohol | 20.0 |
| Ethanol | 20.0 |
| Isoferulic acid | 1.0 |
| Glycerine | 5.0 |
| Perfume | 0.3 |
| Water | 53.7 |
| Formulation Example 7 (Oil) | |
| Squalane | 47.0 |
| Castor oil | 47.0 |
| 2-Ethylhexyl isoferulate | 5.0 |
| 4-Isoamyl resorcinol | 0.79 |
| Perfume | 0.2 |
| Antioxidant | 0.01 |

What is claimed is:

1. A skin depigmental composition, comprising a skin depigmenting effective amount of a resorcinol of the formula (1)

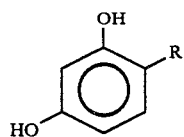

wherein R is a linear alkyl group having from 2-12 carbon atoms or a linear alkyl group having from 2-12 carbon atoms in which a hydrogen atom on the linear alkyl group is substituted by a methyl group, and a cosmetic base.

2. The composition of claim 1, wherein said resorcinol comprises from 0.01-15 wt.% of said composition.

3. The composition of claim 2, wherein said resorcinol comprises 0.1-10 wt.% of said composition.

4. The composition of claim 1, wherein said cosmetic base comprises a cream, ointment, emulsion, lotion, oil or pack.

5. The composition of claim 1, wherein said cosmetic base is beeswax, cetyl alcohol, stearic acid, gylcerine, propylene glycol, propylene glycol monostearate or polyoxyethylene cetyl ether.

6. The composition of claim 1, wherein said cosmetic base is oleyl alcohol, ethanol, lauryl ether or sorbitan monolaurate.

* * * * *